United States Patent [19]
Eriksson et al.

[11] 3,959,476
[45] May 25, 1976

[54] ANTIHYPERTENSIVE SUBSTITUTED TRIAZOLES

[75] Inventors: Hans Erik Eriksson, Holo; Gosta Lennart Florvall, Sodertalje, both of Sweden

[73] Assignee: Astra Lakemedel Aktiebolag, Sodertalje, Sweden

[22] Filed: June 11, 1974

[21] Appl. No.: 478,228

[30] Foreign Application Priority Data
June 14, 1973 Sweden.............................. 7308365 1

[52] U.S. Cl............................. 424/269; 260/240 G; 260/308 R; 424/263
[51] Int. Cl.²................. A61K 31/41; C07D 249/08
[58] Field of Search.................... 260/240 G, 308 R; 424/269

[56] References Cited
UNITED STATES PATENTS
3,516,995  6/1970  Houlihan et al................ 260/240 G
3,775,405  11/1973  Bruce................................ 260/240

OTHER PUBLICATIONS
Wilson & Grisvold, Textbook of Organic Medicinal & Pharmaceutical Chemistry, 4th Ed., pp. 352–356, 1962).

*Primary Examiner*—Leonard Schenkman
*Attorney, Agent, or Firm*—Brumbaugh, Graves, Donohue & Raymond

[57] ABSTRACT
Compounds having the general formula

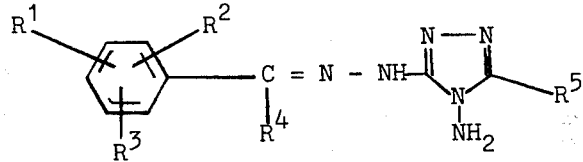

methods for the preparation thereof and use in the treatment of hypertension.

7 Claims, No Drawings

ANTIHYPERTENSIVE SUBSTITUTED TRIAZOLES

This invention relates to new triazoles and methods for their preparation. The invention also relates to the preparation of pharmaceutical preparations containing the triazoles and to methods for the pharmacological use of the triazoles.

PRIOR ART

Hypotensive agents have been known for a considerable time. It has also been known that these agents exert their effects through different mechanisms of action. Side-effects which have clinical implications of major importance are frequently encountered among these compounds. A well-known example is a rise in the blood pressure of shorter or longer duration after administration and before the onset of the desired fall in blood pressure. A further example is the sedative effect of these agents which may make them unsuitable for use by persons who perform any task which requires alertness, for instance car driving.

OUTLINE OF INVENTION a. General outline

We have found that certain compounds related to 4-amino-3-benzylidenehydrazino-1,2,4-triazoles have the ability of lowering the arterial blood pressure of unanesthetized animals with experimentally induced hypertension in oral doses which do not produce sedation or other apparent untoward effects.

More particularly, these compounds have the general formula

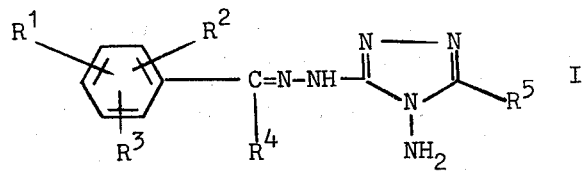

wherein $R^1$, $R^2$ and $R^3$ are the same or different and each represents a hydrogen atom, a lower alkyl group or a halogen atom, $R^4$ represents a hydrogen atom, a lower alkyl group or a pyridyl group and $R^5$ represents a hydrogen atom or a lower alkyl group, provided that $R^4$ is a lower alkyl group or a pyridyl group when $R^1$, $R^2$ and $R^3$ are hydrogen.

The invention also comprises pharmaceutically acceptable salts of the compounds of the formula I.

Illustrative examples of radicals included in the above definitions are pyridyl group: 2-pyridyl lower alkyl group: methyl, ethyl, n-propyl and iso-propyl halogen atom: chlorine, bromine, iodine and fluorine.

By the expression "lower alkyl group" in this application is to be understood alkyl groups with 1, 2 or 3 carbon atoms.

An illustrative example of a compound of the formula I wherein $R^4$ is a lower alkyl group is 4-amino-3-(1-phenylethylidenehydrazino)-1,2,4-triazole.

b. Pharmaceutical preparations

In clinical practice the compounds of the present invention will normally be administered orally, rectally or by injection, in the form of pharmaceutical preparations comprising the active ingredient either as a free base or as a pharmaceutically acceptable non-toxic, acid addition salt, e.g. the hydrochloride, hydrobromide, lactate, acetate, sulphate, sulphamate, and the like, in association with a pharmaceutically acceptable carrier. Accordingly, terms relating to the novel compounds of this invention whether generically or specifically are intended to include both the free amine base and the acid addition salts of the free base, unless the context in which such terms are used, e.g. in the specific examples would be inconsistent with the broad concept. The carrier may be a solid, semisolid or liquid diluent or capsule. These pharmaceutical preparations constitute a further aspect of this invention. Usually the active substance will constitute between 0.1 and 95% by weight of the preparation, more specifically between 0.5 and 20% by weight for preparations intended for injection and between 2 and 50% by weight for preparations suitable for oral administration.

To produce pharmaceutical preparations containing a compound of the invention in the form of dosage units for oral application, the selected compound may be mixed with a solid pulverulent carrier e.g. lactose, saccharose, sorbitol, mannitol, starches such as potato starch, corn starch or amylopectin, cellulose derivatives, or gelatine, and a lubricant such as magnesium stearate, calcium stearate, polyethylene glycol waxes, and the like, and then compressed to form tablets. If coated tablets are required, the cores, prepared as described above, may be coated with a concentrated sugar solution which may contain e.g. gum arabic, gelatine, talcum, titanium dioxide, and the like. Alternatively, the tablet can be coated with a lacquer dissolved in a readily volatile organic solvent or mixture of organic solvents. Dyestuffs may be added to these coatings in order to readily distinguish between tablets containing different active substances or different amount of the active compound.

For the preparation of soft gelatine capsules (pearl-shaped closed capsules) consisting of gelatine, and for example, glycerol or similar closed capsules, the active substance may be admixed with a vegetable oil. Hard gelatine capsules may contain granulates of the active substance in combination with solid, pulverulent carriers such as lactose, saccharose, sorbitol, mannitol, starches (e.g. potato starch, corn starch or amylopectin), cellulose derivatives or gelatine.

Dosage units for rectal application can be prepared in the form of suppositories comprising the active substance in admixture with a neutral fatty base, or gelatine rectal capsules comprising the active substance in admixture with vegetable oil or paraffin oil.

Liquid preparations for oral application may be in the form of syrups or suspensions for example, solutions containing from about 0.2% to about 20% by weight of the active substance herein described, the balance being sugar and a mixture of ethanol, water, glycerol, and propyleneglycol. Optionally, such liquid preparations may contain coloring agents, flavoring agents, saccharine and carboxymethylcellulose as a thickening agent.

Solutions for parenteral applications by injection can be prepared in an aqueous solution of a water-soluble pharmaceutically acceptable salt of the active substance preferably in a concentration of from about 0.5% to about 10% by weight. These solutions may also contain stabilizing agents and/or buffering agents and may conveniently be provided in various dosage unit ampoules.

In therapeutical treatment the suitable diurnal doses of the compounds of the invention are dependent on such factors as, for instance, age and size of the patient and ways of administration.

c. Preferred embodiment

The preferred compound of the invention has the structural formula

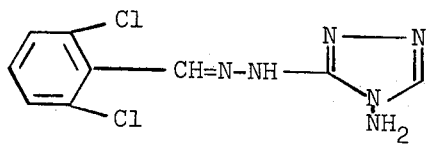
IA

Preferably this compound will be prepared and used in the form of its hydrochloride salt.

d. Methods of preparation

1. Generally, the compounds of the formula I are prepared by treating a benzaldehyde or a ketone of the formula

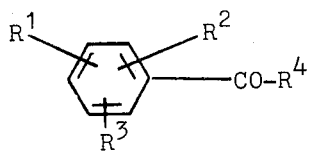
II wherein $R^1$, $R^2$, $R^3$ and $R^4$ are as previously described, with the free base or a salt of the substituted 4-amino-3-hydrazino-1,2,4-triazole of the formula

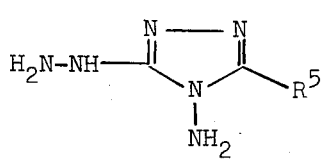
III wherein $R^5$ is as previously described.

The condensation is performed essentially as described in the literature (Ann. 664, 147 (1963); J. Org. Chem. 30, 711 (1965); Acta Pharm. Suecica 7, 87 (1970)). The reaction is carried out at elevated temperatures in a suitable solvent such as ethanol, preferably in acid pH. The aldehydes may not be isolated, but treated in situ with triazoles of formula III. In weak HCl-medium I is formed as the hydrochloride. Other salts which may be used include the strong mineral acid salts, e.g. the hydrogen halides or sulphate and the like. The resulting product is readily recovered by conventional techniques, e.g. filtration. The acid addition salt may be converted to the free base by standard methods. The intermediates of formula II and III are known or may be prepared according to standard methods (Ann. 664, 147 (1963); J. Org. Chem. 30, 711 (1965) Acta Pharm, Suecica 9, 513 (1972).

2. Compounds of the formula I wherein $R^5$ is a hydrogen atom can also be prepared by treating a compound of the formula

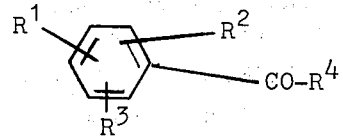
II wherein $R^1$, $R^2$, $R^3$ and $R^4$ are as previously described with a salt of triaminoguanidine in boiling formic acid.

e. Working examples

This invention is further illustrated by the following examples.

EXAMPLE 1

4-Amino-3-(2-methylbenzylidenehydrazino)-1,2,4-triazole hydrochloride (Compound I).

To a solution of 14.0 g (0.075 mole) of 4-amino-3-hydrazino-1, 2,4-triazole dihydrochloride in 200 ml of 75 percent ethanol was added 9.0 g (0.075 mole) of o-tolualdehyde. The mixture was stirred and heated at reflux for 1.5 hour. The solution was cooled and the precipitate formed collected by filtration and washed with ether. Yield: 18.4 g, m.p. 230°–232° (D). After recrystallization from aqueous ethanolisopropyl ether the product melts at 233°–234° (D).

EXAMPLE 2 a. 4-Amino-3-(2,6-dichlorobenzylidenehydrazino)-1,2,4-triazole hydrochloride (Compound VI). Method 1.

To a solution of 7.5 g (0.04 mole) of 4-amino-3-hydrazino-1,2,4-triazole dihydrochloride in 150 ml of 75 percent ethanol was added 7.0 g (0.04 mole) of 2,6-dichlorobenzaldehyde. The mixture was stirred and heated at reflux for 16 hours. The solution was cooled and the crystallization was brought about by the addition of ether. The precipitate was filtered off and washed with ether. Yield: 10.2 g, m.p. 219°–220° (D).

38.0 g of the hydrochloride yielded when treated with 17.0 g sodium hydrogen carbonate in 1000 ml of water, 28.2 g (84%) of the free base, melting at 198°–199°. Equivalent weight: Calc. 271.12, found 273.

The free base was converted to the bisulphate salt by dissolving 8.5 g of the base in 50 ml of acetic acid and treating the solution with 10 ml of concentrated sulphuric acid. 400 ml of ether was added and the obtained precipitate (10.4 g) was recrystallized from ethanol-isopropyl ether yielding 4.5 g of the pure salt, melting at 208°–209° (D), anal. calc. for $C_9H_9Cl_2N_6 \cdot H_2SO_4$: C 29.28, H 2.73, N 22.76, S 8.69. Found: C 28.7, H 2.9, N 22.5, S 8.6.

b. 4-Amino-3-(2,6-dichlorobenzylidenehydrazino)-1,2,4-triazole hydrochloride (Compound VI) Method 2.

To a solution of 7.0 g (0.05 mole) triaminoguanidine hydrochloride in a mixture of 50 ml of formic acid and 10 ml of water was added 8.5 g (0.049 mole) of 2,6-dichlorobenzaldehyde. The mixture was stirred and refluxed for 6 hours. 40 ml of concentrated hydrochloric acid was then added and the mixture was refluxed for 0.5 hour. The solution was evaporated under reduced pressure and the residue was recrystallized from ethanol-isopropyl ether. Yield: 12.2 g (82%) m.p. 217°–218° (D). One more recrystallization from the same solvent gave 9.7 g of an analytically pure sample, m.p. 218°–219° (D).

was added dropwise while stirring and cooling a mixture of 50 ml of concentrated hydrochloric acid and 50 ml of water. The stirring was continued for 30 minutes. The ether layer was separated and the ether removed by evaporating. To the residue was added a solution of 9.35 g (0.05 mole) 4-amino-3-hydrazino-1,2,4-triazole dihydrochloride in 130 ml of 75 percent ethanol. The mixture was stirred and heated at reflux for 5 hours. 600 ml of ethanol was added and the solution cooled. After filtration and evaporation of the solvent 3.6 g of the crude salt was obtained. After recrystallization from ethanol-2N hydrochloric acid, the product melts at 219°–220° (D).

In table 1 are given data for some compounds of this invention including those described in Examples 1–4.

Table 1

4-amino-3-benzylidenehydrazino-1,2,4-triazole hydrochlorides

| Compound No. | $R_1$ | $R_2$ | $R_3$ | $R_4$ | $R_5$ | Reaction time h | M.p. °C | Yield % | Analysis: calc % found % | | | |
|---|---|---|---|---|---|---|---|---|---|---|---|---|
| | | | | | | | | | C | H | N | Cl |
| I | 2-CH₃ | H | H | H | H | 1.5 | 233–34 | 97 | 47.72 | 4.81 | 33.39 | 14.09 |
| | | | | | | | | | 47.7 | 4.9 | 33.5 | 14.0 |
| II | 2-CH₃ | 6-CH₃ | H | H | H | 5 | 219–20 | 27 | 49.53 | 5.67 | 31.51 | 13.29 |
| | | | | | | | | | 49.3 | 5.78 | 31.2 | 13.1 |
| III | 2-CH₃ | 4-CH₃ | 6-CH₃ | H | H | 3 | 218–19 | 57 | 51.33 | 6.10 | 29.93 | 12.63 |
| | | | | | | | | | 51.2 | 6.3 | 29.4 | 12.7 |
| IV | 2-Cl | H | H | H | H | 0.5 | 249–50 | 92 | 39.58 | 3.69 | 30.77 | 25.96 |
| | | | | | | | | | 39.5 | 3.70 | 30.4 | 25.8 |
| V | 2-Cl | 4-Cl | H | H | H | 2.5 | 270–71 | 89 | 35.14 | 2.95 | 27.33 | 34.58 |
| | | | | | | | | | 35.4 | 2.94 | 27.1 | 34.6 |
| VI | 2-Cl | 6-Cl | H | H | H | 16 | 219–20 | 83 | 35.14 | 2.95 | 27.33 | 34.58 |
| | | | | | | | | | 34.8 | 3.05 | 27.3 | 34.4 |
| VII | 2-Cl | 6-Cl | H | H | CH₃ | 16 | 244–45 | 68 | 37.34 | 3.45 | 26.13 | 33.07 |
| | | | | | | | | | 37.3 | 3.33 | 25.9 | 33.2 |
| VIII | 2-Cl | 6-Cl | H | H | C₂H₅ | 16 | 224–25 | 56 | 39.36 | 3.90 | 25.04 | 31.69 |
| | | | | | | | | | 39.4 | 3.96 | 25.1 | 31.4 |
| IX[a] | H | H | H | (pyridyl) | H | 2 | 220–21 | 65 | 45.41 | 4.63 | 26.48 | 19.15 |
| | | | | | | | | | 45.2 | 4.79 | 26.0 | 19.0 |

[a] The compound was obtained as a dihydrochloride monohydrate. Cal.: O 4.32. Found: O 4.49.

EXAMPLE 3

4-Amino-3-(2,6-dichlorobenzylidenehydrazino)-5-methyl-1,2,4-triazole hydrochloride (Compound VII).

To a solution of 5.25 g (0.032 mole) of 4-amino-3-hydrazino-5-methyl-1,2,4-triazole hydrochloride in 100 ml of 75 percent ethanol was added 5.6 g (0.032 mole) of 2,6-dichlorobenzaldehyde and 0.5 ml of concentrated hydrochloric acid. The mixture was stirred and heated at reflux for 16 hours. After cooling, the precipitate was collected and washed with chilled ethanol and ether. Yield: 7.0 g, m.p. 244°–245° (D).

EXAMPLE 4

4-Amino-3-(2,6-dimethylbenzylidenehydrazino)-1,2,4-triazole hydrochloride (Compound II).

In an atmosphere of dry nitrogen, a solution of 9.25 g (0.05 mole) of 2,6-dimethylbromobenzene in 100 ml of ether was added dropwise with stirring to 1.2 g (0.05 g atom) of magnesium turnings in 20 ml of ether. The reaction was started by the addition of ethyl bromide and a crystal of iodine. When all the halide had been added, the solution was refluxed for 2 hours. 8.2 ml (0.052 mole) of triethyl orthoformate was added dropwise and the reaction mixture was refluxed for 1.5 hour and left overnight at room temperature. To the solution f. Biological tests

A comparison of the pharmacological effects of the compound of the invention with the designation FLA 136 having the formula

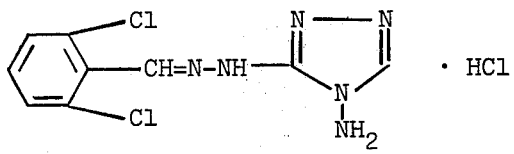

with those of Wy-8678, a well-known hypotensive agent [Experientia (Basel) 25, 1066 (1969)], is presented in table 2.

The hydrochloride salt of Wy-8678, which is used in the tests described below has the formula

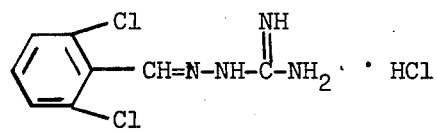

The antihypertensive effects were tested in rats in which high blood pressure had been produced by removal of one kidney and restricting the blood flow to the remaining one two month before the experiments. The animals were prepared for measurements of the arterial blood pressure through a catheter implanted into the abdominal aorta and exteriorized at the base of the neck. Groups of two rats were given three consecutive daily oral doses of the test compounds from the scale: 2.5, 5, 10, 20, and 40 mg/kg. Measurements were performed before and three hours after administration to the unanaesthetized animal. The minimum daily oral dose with antihypertensive effect was defined as the dose which reduced the mean arterial blood pressure more than 15 mm Hg. It can be seen from table 2 that the antihypertensive effects of the test compound of the invention is of the same degree as that of one of the present known most active hypotensive compounds.

The effects on the spontaneous motor activity was tested in mice. Groups of six animals were given the test compounds intraperitoneally one and three hours before test. The animals were placed individually in an activity meter and the activity was recorded for ten minutes. The dose which reduced the spontaneous motor activity to 50 percent of that of control mice was calculated. The lack of sedative effects of the test compound of the invention as compared to Wy-8678 is evident from table 2.

Intravenous administration of consecutive increasing doses of the test compound of the invention and Wy-8678 to anaesthetized rats showed that the test compound of the invention did not produce an initial rise in blood pressure even at 40 mg/kg which was the highest dose tested. Wy-8678 on the other hand produced a large increase in arterial pressure even at doses as low as 0.01 mg/kg.

Table 2

| Pharmacological effects of 4-amino-3-(2,6-dichlorobenzylidenehydrazino)-1,2,4-triazole hydrochloride (FLA 136), a compound according to the invention, and Wy-8678, a reference substance | | |
|---|---|---|
| | FLA 136 (mg/kg) | Wy-8678 (mg/kg) |
| Minimum daily oral dose with antihypertensive effects defined as the dose which reduced the mean arterial blood pressure more than 15 mm Hg in unanaesthetized renal hypertensive rats | 2.5–5 | 2.5 |
| Acute toxicity in mice ($LD_{50}$ i.p.) | 340 | 70 |
| The intraperitoneal dose which reduced the spontaneous motor activity of mice to 50 % of control values | | |
| a) measurements one hour after administration | 90 | 3 |
| b) measurements three hours after administration | 170 | 3 |

We claim:
1. A compound of the formula

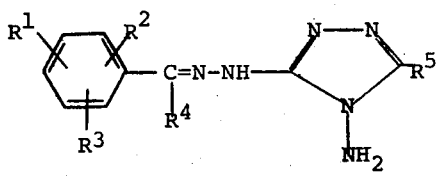

or a pharmaceutically acceptable salt thereof in which formula $R^1$, $R^2$ and $R^3$ are the same or different and each represents a hydrogen atom, a lower alkyl group or a halogen atom, $R^4$ represents a hydrogen atom or a lower alkyl group and $R^5$ represents a hydrogen atom or a lower alkyl group, provided that $R^4$ is a lower alkyl group when $R^1$, $R^2$ and $R^3$ are all hydrogen.

2. A compound according to claim 1 characterized by the formula I, or a pharmaceutically acceptable salt thereof, in which formula $R^1$, $R^2$ and $R^3$ are the same or different and each represents a hydrogen atom, a lower alkyl group or a halogen atom, $R^4$ represents a hydrogen atom and $R^5$ represents a hydrogen atom, provided that $R^1$, $R^2$ and $R^3$ are not all simultaneously hydrogen.

3. A compound according to claim 1 characterized by the formula

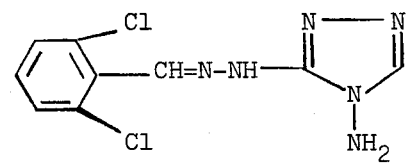

or a pharmaceutically acceptable salt thereof.

4. An antihypertensive pharmaceutical preparation which comprises as active ingredient from 0.1% to 95% by weight of said preparation of a compound of the formula

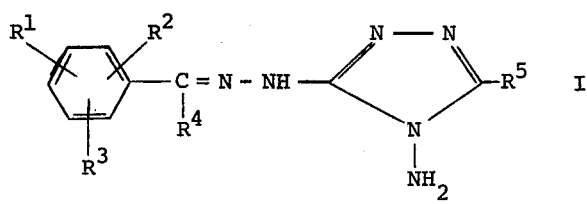

or a pharmaceutically acceptable salt thereof in which formula $R^1$, $R^2$ and $R^3$ are the same or different and each represents a hydrogen atom, a lower alkyl group or a halogen atom, $R^4$ represents a hydrogen atom or a lower alkyl group and $R^5$ represents a hydrogen atom or a lower alkyl group, provided that $R^4$ is a lower alkyl group when $R^1$, $R^2$ and $R^3$ are all hydrogen, in association with a pharmaceutically acceptable carrier.

5. An antihypertensive pharmaceutical preparation according to claim 4 wherein $R^1$, $R^2$ and $R^3$ are the same or different and each represents a hydrogen atom, a lower alkyl group or a halogen atom, $R^4$ represents a hydrogen atom and $R^5$ represents a hydrogen atom, provided that $R^1$, $R^2$ and $R^3$ are not all simultaneously hydrogen.

6. A method for the treatment of hypertension, which comprises administration to a host suffering from such ailment an antihypertensive pharmaceutical preparation which comprises, as active ingredient, a therapeutically acceptable amount of a compound of the formula

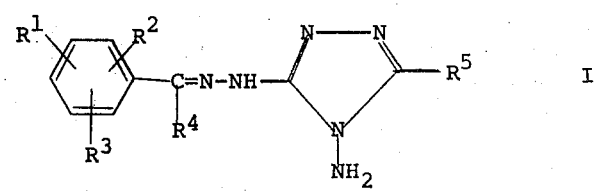

or a pharmaceutically acceptable salt thereof in which formula $R^1$, $R^2$ and $R^3$ are the same or different and each represents a hydrogen atom, a lower alkyl group or a halogen atom, $R^4$ represents a hydrogen atom or a lower alkyl group and $R^5$ represents a hydrogen atom or a lower alkyl group, provided that $R^4$ is a lower alkyl group when $R^1$, $R^2$ and $R^3$ are all hydrogen.

7. A method according to claim 6, wherein $R^1$, $R^2$ and $R^3$ are the same or different and each represents a hydrogen atom, a lower alkyl group or a halogen atom, $R^4$ represents a hydrogen atom and $R^5$ represents a hydrogen atom, provided that $R^1$, $R^2$ and $R^3$ are not all simultaneously hydrogen.

* * * * *